(12) United States Patent
Goetze et al.

(10) Patent No.: US 7,211,683 B2
(45) Date of Patent: May 1, 2007

(54) PROCESS FOR PREPARING ORGANOSILANES

(75) Inventors: Ulrich Goetze, Burghausen (DE); Michael Hansel, Mauerkirchen (DE); Edgar Schmidt, Burghausen (DE); Norbert Zeller, Burghausen (DE)

(73) Assignee: Wacker Chemie AG, Munich (DE)

( * ) Notice: Subject to any disclaimer, the term of this patent is extended or adjusted under 35 U.S.C. 154(b) by 168 days.

(21) Appl. No.: 10/971,811

(22) Filed: Oct. 22, 2004

(65) Prior Publication Data

US 2005/0137413 A1 Jun. 23, 2005

(30) Foreign Application Priority Data

Oct. 23, 2003 (DE) ............................. 103 49 286

(51) Int. Cl.
 *C07F 7/04* (2006.01)
(52) U.S. Cl. .................................................... 556/473
(58) Field of Classification Search ................. 556/473
See application file for complete search history.

(56) References Cited

U.S. PATENT DOCUMENTS 5,502,230 A * 3/1996 Mautner et al. ............. 556/468
6,175,030 B1 * 1/2001 Kalchauer et al. .......... 556/472

FOREIGN PATENT DOCUMENTS

DE 2 132 569 2/1972
SU 491641 * 11/1975

OTHER PUBLICATIONS

Clarke et al. The role of silylenes in the direct synthesis of methylchlorosilanes, Journal of Organometallic Chemistry, 1991, 408 (2), 149-156.*
W. Noll., "Chemistry and Technology of Silicones," Academic Press Inc., Orlando 1968, pp. 26-28.
R.J.H. Voorhoeve, "Organohalosilanes," Elseviet Publicshing Company 1967, p. 40-48.

* cited by examiner

*Primary Examiner*—Thurman Page
*Assistant Examiner*—Chukwuma Nwaonicha
(74) *Attorney, Agent, or Firm*—Brooks Kushman P.C.

(57) ABSTRACT

The invention relates to a process for preparing organosilanes of the general formula 1

$$R_3Si\text{—}R', \quad (1)$$

in which hydrosilanes of the general formula 2

$$R_3Si\text{—}H \quad (2)$$

are reacted with halohydrocarbons of the general formula 3

$$R'\text{—}X \quad (3)$$

where
R are monovalent $C_1$–$C_{18}$ hydrocarbon radicals, hydrogen or halogen,
R' are monovalent $C_1$–$C_{18}$ hydrocarbon radicals and
X is halogen,
in the presence of a free-radical initiator which is selected from alkanes, diazenes and organodisilanes.

20 Claims, No Drawings

PROCESS FOR PREPARING ORGANOSILANES

BACKGROUND OF THE INVENTION

1. Field of the Invention

The invention relates to a process for preparing organosilanes from hydrosilanes and halohydrocarbons in the presence of a free-radical initiator.

2. Background Art

Processes are known in which the hydrogen in hydrosilanes is replaced by a hydrocarbon radical. The thermally induced reaction of hydrosilanes with halohydrocarbons, and also the reaction in the presence of catalysts, are described, for example, in: ORGANOHALOSILANES, by R. J. H. Voorhoeve, Elsevier Publishing Company 1967, pages 40–48.

Thermal initiation has greater significance in the preparation of phenyltrichlorosilane or phenylmethyldichlorosilane from chlorobenzene and trichlorosilane or dichloromethylsilane. Disadvantageously, lower conversions are obtained in this process at low temperatures and a high proportion of undesired by-products at high temperatures. Phenyltrichlorosilane and phenylmethyldichlorosilane are used to prepare organopolysiloxanes.

DE 2132569 A discloses that these reactions can be initiated by appropriate wavelengths of electromagnetic radiation.

Chem. Abstr. 84: 44 345e further discloses the preparation of organochlorosilanes by reacting chlorine-containing aromatics with hydro- or organohydrochlorosilanes employing hexachlorodisilane as a catalyst. Disadvantageously, the preparation of hexachlorodisilane is costly and inconvenient.

SUMMARY OF THE INVENTION

It is an object of the invention to provide a process for preparing organosilanes having a high space-time yield, in which few undesired by-products are formed, in which damage to the reactors as a result of carbonization and corrosion are low, and the disadvantages of the prior art are avoided.

DETAILED DESCRIPTION OF THE PREFERRED EMBODIMENT(S)

The invention provides a process for preparing organosilanes of the general formula 1

in which hydrosilanes of the general formula 2

are reacted with halohydrocarbons of the general formula 3

where
R are independently monovalent $C_1$–$C_{18}$ hydrocarbon radicals, hydrogen or halogen,
R' are independently monovalent $C_1$–$C_{18}$ hydrocarbon radicals and
X is halogen, in the presence of a free-radical initiator which is selected from alkanes, diazenes and organodisilanes.

Preference is given to using free-radical initiators which decompose below 600° C. within from 3 to 30 seconds, in particular from 5 to 15 seconds.

The free-radical initiators used are preferably alkanes of the general formula 4

where
$R^1$ to $R^6$ are each alkyl radicals or
$R^1$ and $R^4$ are each phenyl radicals and $R^2$, $R^3$, $R^5$ and $R^6$ are each hydrogen or alkyl radicals or
$R^1$ and $R^4$ are each phenyl radicals and $R^2$ and $R^5$ are each phenyl radicals or alkyl radicals and
$R^3$ and $R^6$ are each trialkylsiloxy radicals or
$R^1$, $R^2$, $R^4$, and $R^5$ are each phenyl radicals and $R^3$ and $R^6$ are each hydrogen, alkyl or trialkylsiloxy radicals,
or diazenes of the general formula 5

where $R^7$ and $R^8$ are each $C_1$–$C_{18}$ hydrocarbon radicals, or organodisilanes of the general formula 6

where $R^9$ and $R^{10}$ are each halogen or $C_1$–$C_{18}$ hydrocarbon radicals. Except for the provisos expressly stated above, each of $R^1$ through $R^{10}$ may be the same or different, and more than one of each type of initiator of the formulae (4), (5), and (6), and also mixtures of these types of initiators may be used.

Preferred alkyl radicals in this context are $C_1$–$C_6$-alkyl radicals, in particular methyl, ethyl, and n-propyl radicals, and a preferred trialkylsiloxy radical is the trimethylsiloxy radical.

$R^7$ and $R^8$ are preferably alkyl, aryl or aralkyl radicals.
$R^9$ and $R^{10}$ are preferably $C_1$–$C_6$-alkyl radicals, in particular the methyl radical, the ethyl radical, or chlorine.

Particularly good results are achieved with 1,2-diphenylethane, 2,3-diphenyl-2,3-dimethylbutane, 1,1,2,2-tetraphenylethane, 3,4-dimethyl-3,4-diphenylhexane, dicyclohexyldiazene and di-t-butyldiazene.

The R radicals are preferably phenyl radicals or $C_1$–$C_6$-alkyl radicals, in particular methyl or ethyl radicals, chlorine, or hydrogen.

The R' radicals preferably have C=C double bonds. The R' radicals are preferably alkenyl radicals having preferably from 2 to 6 carbon atoms such as the vinyl, allyl, methallyl, 1-propenyl, 5-hexenyl, ethynyl, butadienyl, hexadienyl, cyclopentenyl, cyclopentadienyl, and cyclohexenyl radicals, preferably vinyl and allyl radicals; aryl radicals such as phenyl radicals; alkaryl radicals, aralkyl radicals, alkenylaryl or arylalkenyl radicals; and phenylalkenyl radicals.

X and R, when halogens, are preferably fluorine, chlorine and bromine, in particular chlorine.

In particular, phenyltrichlorosilane and phenylmethyldichlorosilane are prepared from the corresponding hydrosilanes of the general formula 2 by reaction with chlorobenzene.

In the preparation of phenylmethyldichlorosilane by reacting chlorobenzene with dichloromethylsilane in a preferred embodiment of the process of the invention, the high-boiling fraction from the distillation residue of the Rochow synthesis of dichlorodimethylsilane (W. Noll, CHEMISTRY AND TECHNOLOGY OF SILICONES, Academic Press Inc. Orlando 1968, pages 26–28) having the approximate composition $(CH_3)_{2.6}Si_2Cl_{3.4}$ and similar residues are used as the organodisilane component. In addition to the main constituents, trimethyltrichlorodisilane and dimethyltetrachlorodisilane, small amounts of tetramethyldisilane, dimethyldichlorosilane and the corresponding siloxanes in the boiling range from 150 to 160° C. are present. This mixture is referred to hereinbelow as cleavable disilane.

The process according to the invention is preferably carried out at temperatures in the range from 300° C. to 600° C. Preference is given to reacting chlorobenzene with trichlorosilane or dichoromethylsilane in a molar ratio of from 4:1 to 1:4, in particular from 1.5:1.0 to 3.0:1.0. The amount of alkane or diazene used as a free-radical initiator is preferably from 0.005 to 3% by weight, in particular from 0.01 to 0.5% by weight, based on the mixture of chlorobenzene and trichlorosilane or dichloromethylsilane used. When organodisilanes, especially cleavable disilane, are used as the free-radical initiator, preference is given to using from 1 to 15% by weight, in particular from 2 to 10% by weight, based on the mixture of chlorobenzene and trichlorosilane or dichloromethylsilane used.

Preference is given to carrying out the process according to the invention at the pressure of the surrounding atmosphere, i.e. at about 1020 hPa. However, higher pressures may also be employed if appropriate.

The process according to the invention is preferably carried out in a tubular reactor made of steel, and the mixture of hydrosilanes of the general formula 2 and halohydrocarbons of the general formula 3, preferably a mixture of chlorobenzene and trichlorosilane or dichloromethylsilane and free-radical initiator, is preferably fed in in vaporous form. To this end, the liquid components may be passed through an evaporator and the vapors subsequently through a heat exchanger, so that they enter the reactor zone at approximately the desired reaction temperature. This arrangement further ensures that ordinarily non-volatile initiators are also transported into the reactor. In a preferred embodiment, free-radical initiators which are solid at room temperature are used in the form of a solution in chlorobenzene. The residence time of the reaction mixture in the reactor is preferably from 2 to 80 seconds, in particular from 5 to 50 seconds.

All aforementioned symbols of the aforementioned formulae are each defined independently of one another.

In the examples which follow, unless stated otherwise in each case, all amount and percentage data are based on weight, all pressures are 0.10 MPa (abs.) and all temperatures are 20° C.

EXAMPLES 1 TO 10

In a tubular reactor made of steel, chlorobenzene and trichlorosilane (Examples 1 to 6, Table 1) or dichloromethylsilane (Examples 7 to 10, Table 2) are fed in vaporous form with the free-radical initiators indicated, in the quantitative ratios reported. The components were first directed through an evaporator and the vapors subsequently through a heat exchanger, so that they enter the reaction zone at approximately the reaction temperature. The residence time was 5 seconds. Examples 1a, 1b, and 1c are Comparative Examples, as are also Examples 7a, 7b, and 7c.

TABLE 1

Molar chlorobenzene:trichlorosilane ratio 1:2.4
0.7% by weight of free-radical initiator

| Example | Free-radical initiator | Temperature (° C.) | Space-time output (kg/m³ · h) | Amount of waste (kg/kg of product) |
|---|---|---|---|---|
| 1a | | 590 | 120 | 0.51 |
| 1b | | 500 | 15 | 0.38 |
| 1c | | 450 | 0 | — |
| 2a | 1,2-Diphenylethane | 590 | 370 | 0.44 |
| 2b | 1,2-Diphenylethane | 510 | 120 | 0.37 |
| 3a | 2,3-Diphenyl-2,3-dimethylbutane | 590 | 245 | 0.47 |
| 3b | 2,3-Diphenyl-2,3-dimethylbutane | 520 | 120 | 0.31 |
| 3c | 2,3-Diphenyl-2,3-dimethylbutane | 450 | 70 | 0.22 |
| 4a | 1,1,2,2-Tetraphenylethane | 590 | 200 | 0.47 |
| 4b | 1,1,2,2-Tetraphenylethane | 550 | 120 | 0.40 |
| 5a | Azobenzene | 590 | 220 | 0.79 |
| 5b | Azobenzene | 565 | 120 | 0.65 |
| 6 | Di-t-butyldiazene | 300 | 106 | 0.12 |

TABLE 2

Molar chlorobenzene:dichloromethylsilane ratio 1:2.5

| Example | Free-radical initiator | % by wt. of free-radical initiator | Temperature (° C.) | Space-time output (kg/m³ · h) | Amount of waste (kg/kg of product) | Contamination of $PhSiCl_3$ in the product (% by wt.) |
|---|---|---|---|---|---|---|
| 7a | — | | | | 1.4 | 6.0 |
| 7b | — | | 540 | 50 | 1.0 | 1.5 |
| 7c | — | | 500 | 5 | — | |
| 8a | Cleavable disilane | 5 | 590 | 160 | 1.4 | 4.0 |
| 8b | Cleavable disilane | 15 | 590 | 140 | 2.0 | 14.0 |
| 9a | Cleavable disilane | 5 | 570 | 90 | 1.2 | 6.0 |
| 9b | Cleavable disilane | 5 | 540 | 110 | 1.0 | 1.2 |
| 10 | 2,3-Diphenyl-2,3-dimethylbutane | 0.7 | 590 | 120 | 1.2 | 2.5 |

EXAMPLES 11–12

In a tubular reactor made of steel, chlorobenzene and trichlorosilane in a molar ratio of 2:1 were fed in vaporous form, and, in Example 11, a 10% solution of 1,2-diphenylethane in chlorobenzene was additionally used in such an amount that the mixture of trichlorosilane and chlorobenzene contained 0.02% by weight of this free-radical initiator. The components were first directed through an evaporator and the vapors subsequently through a heat exchanger, so that they entered the reaction zone at approximately the reaction temperature. The residence time was 20 seconds, the temperature 550° C.

EXAMPLE 11

The reaction mixture contained 33.04% by weight of phenyltrichlorosilane; the ratio of undesired by-products/target product was 0.41.

EXAMPLE 12

Noninventive, Without Free-radical Initiator

The reaction mixture contained 22.17% by weight of phenyltrichlorosilane; the ratio of undesired by-products/target product was 0.48.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing organosilanes of the formula 1

$R_3Si—R'$ (1), in which hydrosilanes of the formula 2

$R_3Si—H$ (2)

are reacted with halohydrocarbons of the formula 3

$R'—X$ (3)

where
R are independently monovalent $C_1$–$C_{18}$ hydrocarbon radicals, hydrogen or halogen,
R' are independently monovalent $C_1$–$C_{18}$ hydrocarbon radicals, and
X is halogen,
in the presence of a free-radical initiator which is selected from alkanes, diazenes and organodisilanes.

2. The process of claim 1, in which free-radical initiators are used which decompose below 600° C. within from 3 to 30 seconds.

3. The process of claim 1 in which the free-radical initiators used are alkanes of the formula 4

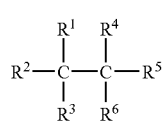

(4)

where
$R^1$ to $R^6$ are each independently alkyl radicals, or
$R^1$ and $R^4$ are each phenyl radicals and $R^2$, $R^3$, $R^5$ and $R^6$ are each independently hydrogen or alkyl radicals, or
$R^1$ and $R^4$ are each phenyl radicals and $R^2$ and $R^5$ are each independently phenyl radicals or alkyl radicals, and $R^3$ and $R^6$ are each trialkylsiloxy radicals, or
$R^1$, $R^2$, $R^4$, and $R^5$ are each phenyl radicals and $R^3$ and $R^6$ are each independently hydrogen, alkyl or trialkylsiloxy radicals; or
diazenes of the general formula 5

$R^7—N=N—R^8$ (5)

where $R^7$ and $R^8$ are each independently $C_1$–$C_{18}$ hydrocarbon radicals; or
organodisilanes of the general formula 6

$R^9_3Si—SiR^{10}_3$ (6)

where $R^9$ and $R^{10}$ are each independently halogen or $C_1$–$C_{18}$ hydrocarbon radicals.

4. The process of claim 2 in which the free-radical initiators used are alkanes of the formula 4

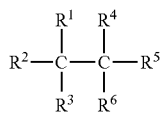

(4)

where
$R^1$ to $R^6$ are each independently alkyl radicals, or
$R^1$ and $R^4$ are each phenyl radicals and $R^2$, $R^3$, $R^5$ and $R^6$ are each independently hydrogen or alkyl radicals, or
$R^1$ and $R^4$ are each phenyl radicals and $R^2$ and $R^5$ are each independently phenyl radicals or alkyl radicals, and $R^3$ and $R^6$ are each trialkylsiloxy radicals, or
$R^1$, $R^2$, $R^4$, and $R^5$ are each phenyl radicals and $R^3$ and $R^6$ are each independently hydrogen, alkyl or trialkylsiloxy radicals; or
diazenes of the general formula 5

$R^7—N=N—R^8$ (5)

where $R^7$ and $R^8$ are each independently $C_1$–$C_{18}$ hydrocarbon radicals; or
organodisilanes of the general formula 6

$R^9_3Si—SiR^{10}_3$ (6)

where $R^9$ and $R^{10}$ are each independently halogen or $C_1$–$C_{18}$ hydrocarbon radicals.

5. The process of claim 1, wherein at least one $R_3SiR^1$ is phenyltrichlorosilane or phenylmethyldichlorosilane.

6. The process of claim 2, wherein at least one $R_3SiR^1$ is phenyltrichlorosilane or phenylmethyldichlorosilane.

7. The process of claim 3, wherein at least one $R_3SiR^1$ is phenyltrichlorosilane or phenylmethyldichlorosilane.

8. The process of claim 4, wherein at least one $R_3SiR^1$ is phenyltrichlorosilane or phenylmethyldichlorosilane.

9. The process of claim 5, in which chlorobenzene is reacted with trichlorosilane or dichloromethylsilane in a molar ratio of from 4:1 to 1:4.

10. The process of claim 5, wherein the reaction takes place at a temperature in the range from 300° C. to 600° C.

11. The process of claim 9, wherein the reaction takes place at a temperature in the range from 300° C. to 600° C.

12. The process of claim 1, wherein said free radical initiator comprises a cleavable disilane mixture from the Rochow synthesis of dichlorodimethylsilane.

13. The process of claim 2, wherein said free radical initiator comprises a cleavable disilane mixture from the Rochow synthesis of dichlorodimethylsilane.

14. The process of claim 5, wherein said free radical initiator comprises a cleavable disilane mixture from the Rochow synthesis of dichlorodimethylsilane.

15. The process of claim 9, wherein said free radical initiator comprises a cleavable disilane mixture from the Rochow synthesis of dichlorodimethylsilane.

16. The process of claim 10, wherein said free radical initiator comprises a cleavable disilane mixture from the Rochow synthesis of dichlorodimethylsilane.

17. The process of claim 12, wherein the cleavable disilane is a residue having an approximate composition of $(CH_3)_{2.6}Si_2Cl_{3.4}$.

18. A process for preparing organosilanes of the formula 1

$$R_3Si—R' \qquad (1),$$

in which hydrosilanes of the general formula 2

$$R_3Si—H \qquad (2)$$

are reacted with halohydrocarbons of the general formula 3

$$R'—X \qquad (3)$$

where
- R are monovalent $C_1$–$C_{18}$ hydrocarbon radicals, hydrogen or halogen,
- R' are monovalent $C_1$–$C_{18}$ hydrocarbon radicals and
- X is halogen, in the presence of a free-radical initiator which is selected from alkanes, diazenes.

19. The process of claim 18, wherein at least one free radical initiator is selected from the group consisting of 1,2-diphenylethane, 2,3-diphenyl-2,3-dimethylbutane, 1,1,2,2-tetraphenylethane, 3,4-dimethyl-3,4-diphenylhexane, dicyclohexyldiazene and di-t-butyldiazene.

20. The process of claim 18, wherein the organosilane 1 comprises phenyltrichiorosilane, phenylmethyldichlorosilane, or mixtures thereof.

* * * * *

UNITED STATES PATENT AND TRADEMARK OFFICE
CERTIFICATE OF CORRECTION

PATENT NO.       : 7,211,683 B2                                       Page 1 of 1
APPLICATION NO.  : 10/971811
DATED            : May 1, 2007
INVENTOR(S)      : Ulrich Goetze et al.

It is certified that error appears in the above-identified patent and that said Letters Patent is hereby corrected as shown below:

Column 7, Line 13, Claim 18:

Delete "general".

Column 7, Line 16, Claim 18:

Delete "general".

Signed and Sealed this

Fourteenth Day of August, 2007

JON W. DUDAS
*Director of the United States Patent and Trademark Office*